(12) United States Patent
Luther

(10) Patent No.: US 8,608,722 B2
(45) Date of Patent: Dec. 17, 2013

(54) CONTAINER FOR AN ANAL IRRIGATION SYSTEM

(75) Inventor: Preben Luther, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 638 days.

(21) Appl. No.: 12/677,115

(22) PCT Filed: Sep. 18, 2008

(86) PCT No.: PCT/DK2008/050224
§ 371 (c)(1),
(2), (4) Date: Mar. 9, 2010

(87) PCT Pub. No.: WO2009/036765
PCT Pub. Date: Mar. 26, 2009

(65) Prior Publication Data
US 2010/0204681 A1   Aug. 12, 2010

(30) Foreign Application Priority Data
Sep. 21, 2007  (DK) ................................ 2007 01364

(51) Int. Cl.
*A61B 19/00* (2006.01)
(52) U.S. Cl.
USPC ............. 604/406; 604/35; 604/305; 604/306; 604/307; 604/308; 604/313; 604/317; 604/318; 604/319; 604/320; 604/321; 604/322; 604/323; 604/403; 604/540; 604/541; 604/542; 604/543; 604/544; 604/902; 606/131
(58) Field of Classification Search
USPC .................................. 604/403, 406, 540–544
See application file for complete search history.

(56) References Cited

U.S. PATENT DOCUMENTS

| 3,888,235 A | 6/1975 | May et al. |
| 4,014,322 A | 3/1977 | Shah |
| 4,828,546 A | 5/1989 | McNeil et al. |
| 5,201,893 A | 4/1993 | Holloway et al. |
| 5,386,735 A | 2/1995 | Langdon |
| 6,264,636 B1 | 7/2001 | Holm et al. |

(Continued)

FOREIGN PATENT DOCUMENTS

| CN | 2160402 | 4/1994 |
| FR | 1222961 | 6/1960 |

(Continued)

*Primary Examiner* — Tatyana Zalukaeva
*Assistant Examiner* — Ilya Treyger
(74) *Attorney, Agent, or Firm* — Coloplast Corp., Coloplast A/S; Nick Baumann

(57) ABSTRACT

The present invention relates to a container for anal irrigation. In particular it relates to a rigid container which is easy to operate and which easily is transformed from a storage configuration to a ready-to-use configuration. In one aspect the invention relates to a container for an anal irrigation system. The anal irrigation system comprises an anal probe; a reservoir for holding an irrigation liquid (e.g. water); a pump mechanism for pumping a fluid (e.g. air) into the reservoir; and a liquid tube connecting the reservoir with the anal probe. The container comprises an outer chamber wall, defining at least partly the outer dimensions of the container and an inner chamber wall arranged within the outer chamber wall, said outer chamber wall and inner chamber wall defining the reservoir. This provides a reservoir having a small surface area when filled with irrigation liquid. Thus only a low pressure is necessary to evacuate the irrigation liquid from the reservoir and out through the anal probe.

3 Claims, 4 Drawing Sheets

(56) References Cited

U.S. PATENT DOCUMENTS

| | | |
|---|---|---|
| 6,391,010 B1 | 5/2002 | Wilcox |
| 2003/0073963 A1* | 4/2003 | Falconer .................. 604/328 |
| 2005/0215961 A1 | 9/2005 | Romano |

FOREIGN PATENT DOCUMENTS

| | | |
|---|---|---|
| FR | 2750855 | 1/1998 |
| GB | 06031 | 0/1912 |
| GB | 19107 | 0/1913 |
| GB | 137316 | 12/1919 |
| WO | 8800840 | 2/1988 |
| WO | 9414045 | 6/1994 |
| WO | 9838109 | 9/1998 |
| WO | 03030968 | 4/2003 |
| WO | 03030969 | 4/2003 |
| WO | 2004050534 | 6/2004 |

* cited by examiner

CONTAINER FOR AN ANAL IRRIGATION SYSTEM

FIELD OF THE INVENTION

The present invention relates to a container for anal irrigation. In particular it relates to a rigid container which is easy to operate and which easily is transformed from a storage configuration to a ready-to-use configuration.

BACKGROUND

It is known that using anal irrigation regularly can relieve a person of many types of bowel disorders. For example disorders such as constipations and faecal incontinence and may also stimulate the peristaltic of the intestines.

Thus, different types of anal irrigation system have been provided. One such type of system comprises an anal probe for insertion into the rectum. Irrigation liquid can then be injected into the intestines through said anal probe.

The anal probe is connected to a reservoir containing the irrigation liquid via a liquid tube. By using a pump mechanism pressure may be built inside the reservoir, by for example pumping air into the reservoir. This will cause the irrigation liquid to be pushed out through the liquid tube and into the rectum via the anal probe.

However, many known anal irrigation system comprises many different parts, which has to be assembled before the system may be ready to use.

It is such desirable to provide an anal irrigation system that is easy to transform from a storage configuration into a ready-to-use configuration.

SUMMARY OF THE INVENTION

In one aspect the invention relates to a container for an anal irrigation system, said anal irrigation system further comprising an anal probe; a reservoir for holding an irrigation liquid (e.g. water); a pump mechanism for pumping a fluid (e.g. air) into the reservoir; and a liquid tube connecting the reservoir with the anal probe, wherein said container comprises an outer chamber wall, defining at least partly the outer dimensions of the container and an inner chamber wall arranged within the outer chamber wall, said outer chamber wall and inner chamber wall defining the reservoir.

This provides a reservoir having a small surface area when filled with irrigation liquid. Thus only a low pressure is necessary to evacuate the irrigation liquid from the reservoir and out through the anal probe.

The chamber walls may be formed of a rigid material. By rigid it should be understood that the material of the chamber walls is of a type, which will not bend, collapse or otherwise deform under normal operating conditions of the anal irrigation system. Many types of suitable materials for such rigid chamber walls may be found within the group of polypropylenes, or even glass or metal. For example Tupperware® products are typically formed of a plastic material which would be considered rigid for the purpose of anal irrigation, while it still is possible for a person to bend.

However, it should be understood that when pressure is built up inside the reservoir even flexible and collapsible chamber walls will expand into preset shapes. It is in this expanded configuration that the shape of the reservoir influences the amount of pressure necessary to press the irrigation liquid out of the liquid tube and into the rectum via the anal probe. Thus, also flexible, collapsible and otherwise deformable chamber walls may be used for the container.

In one embodiment the reservoir may have a thickness of less than one centimeter. Thus the perpendicular distance between the outer chamber wall and the inner chamber wall does not exceed one centimeter.

In one embodiment, and in particular when the chamber walls is formed of a rigid material the outer chamber wall and inner chamber wall are parallel. This provides for an easy control of much pressure is necessary to push the irrigation liquid out the liquid in a flow, which is sufficient to irrigate the rectum but not so high that it becomes uncomfortable or even harmful to the user.

In another aspect the invention relates to a container for an anal irrigation system, said anal irrigation system further comprising an anal probe; a reservoir for holding an irrigation liquid (e.g. water); a pump mechanism for pumping a fluid (e.g. air) into the reservoir; and a liquid tube connecting the reservoir with the anal probe, wherein said container comprises; an outer chamber wall at least partly defining the reservoir; a lid for at least partly closing one end of said container thereby defining the reservoir; a first through going hole provided in the lid; that the liquid tube is arranged so that it communicates through the first through going hole in a liquid tight manner; and a second opening providing fluid communication between the pump mechanism and the reservoir.

This allows for a lid, which may be reversible, i.e. the lid may be attachable to the container in at least two different configurations. This allows for the anal irrigation system to be transformed from a storage configuration wherein it may be safely transported or stored; into a use configuration wherein it is ready for anal irrigation, by a single and intuitive motion.

In the storage configuration the lid is so oriented and attached to the outer chamber wall that the first liquid tube extends from the first through going towards the pump unit inside the reservoir. In the use configuration the liquid tube extends towards the pump unit outside the reservoir.

In one embodiment a first end of the liquid tube is attached around the first through going hole on one side of the lid, in order to provide a liquid and fluid tight communication with the reservoir.

Alternatively the liquid tube may be slideable engaged through the first through going hole.

As described above the chamber wall may be formed of a rigid material. However it should be understood that when pressure is built up inside the reservoir even flexible and collapse able chamber walls would expand into preset shapes. It should be understood that in order to fix/equip a lid on a collapsible container that a stiff area around the opening is provided wherein the lid could be attached in a liquid and fluid tight manner.

DETAILED DESCRIPTION

Figure 1:
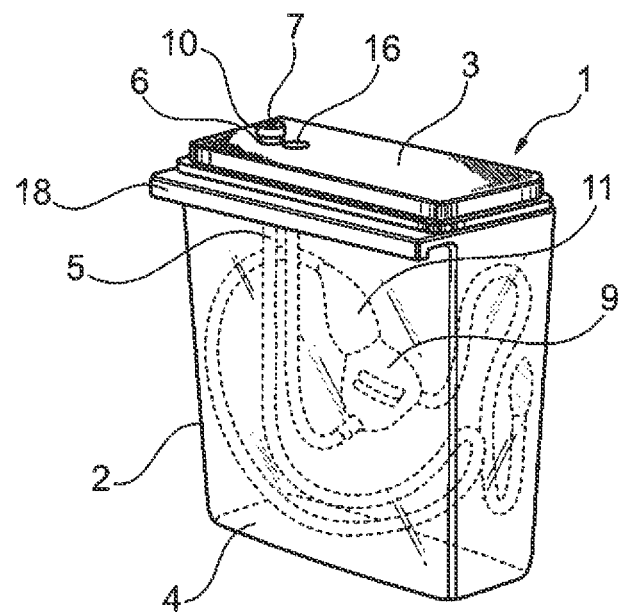
FIG. 1-3 shows a first embodiment of a container according to the invention in different configurations.
Figure 2:
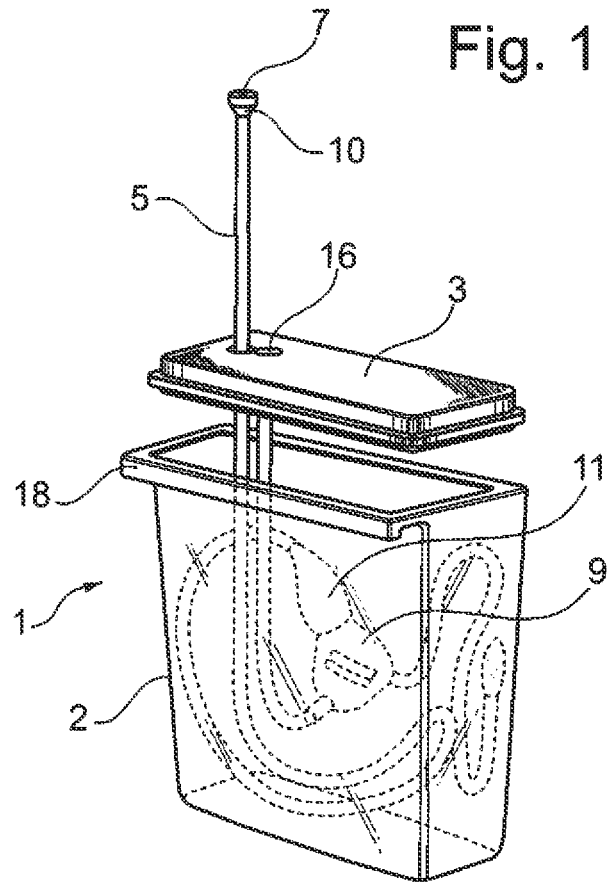
Figure 3:
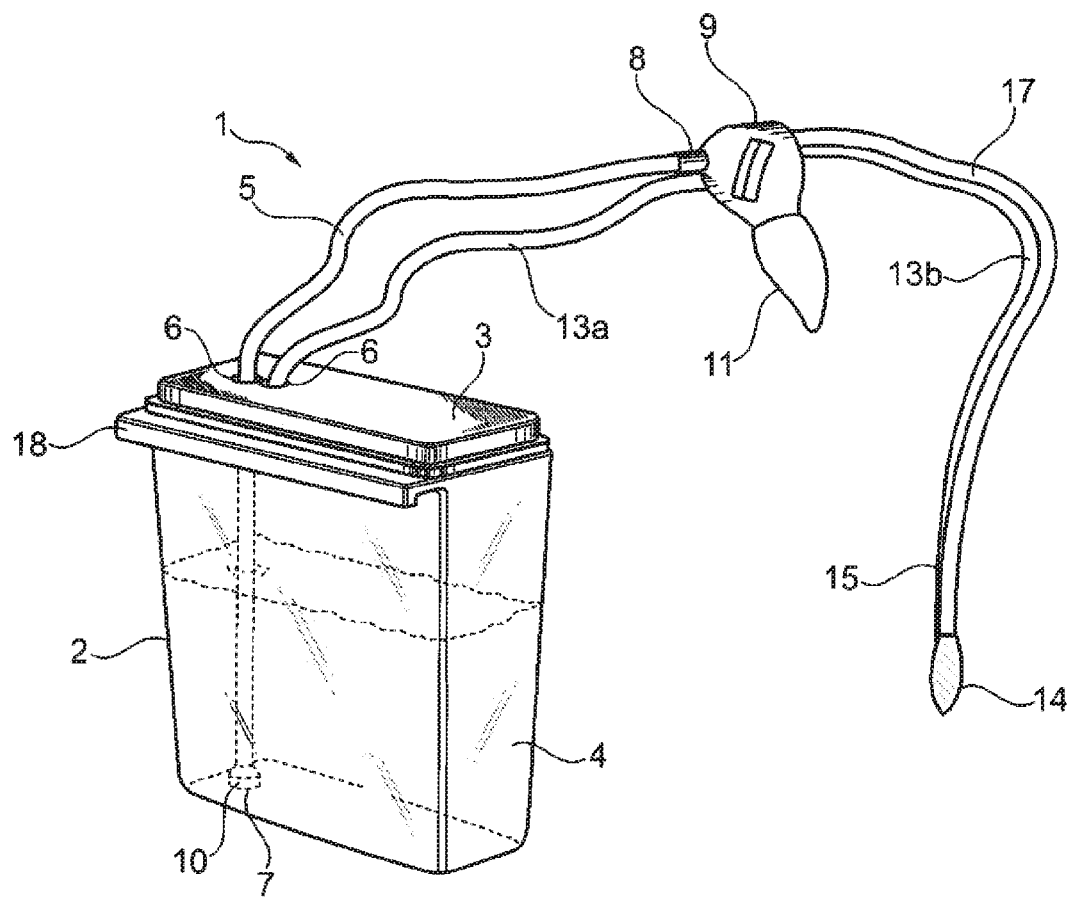

FIG. 1-3 shows the use of an anal irrigation system 1 according to the invention.

The anal irrigation system comprises a container 2, a lid 3 for closing said container and thereby defining a closed reservoir 4. A first liquid tube 5 is slideably arranged in a first through going hole 6 provided in the lid 3.

The first liquid tube extends from a first free end 7 to a second end 8, which is connected to a pump unit 9. The first free end is provided with a protruding rim 10 which have a diameter larger than the diameter of the first through going hole. This prevents the first free end 7 to be pulled through the first through going hole 6.

The first through going hole is provided with sealing means (not shown) for providing a liquid and fluid tight seal between the first through going hole and the first liquid tube. An o-ring, an annular lip or similar known means, can for example provide such sealing means. The sealing means are capable of providing a liquid and fluid tight seal while the reservoir is pressurized within the normal ranges used within anal irrigation system. During normal operation the reservoir is capable of handling a pressure, which corresponds to lifting a water column of irrigation liquid within the liquid hose, which is a meter and a half.

The pump unit 9 comprises a manual pump 11 and a control unit 12. The control unit 12 allows the user to decide whether a fluid (typically air) should be pumped from the manual pump 11 into a first fluid tube 13a (referred to as the first position of the control unit), which is connected to the lid; or into a second fluid tube 13b (referred to as the second position of the control unit), which provides fluid passage to a balloon 14 on a anal probe in the form of a balloon catheter 15.

As mentioned, the first fluid tube is connected to the lid 13. It is attached to the lid around a second through going hole 16 through air may pass when a user uses the manual pump and the control unit is in its first position.

The balloon catheter 15 is fluidly connected to a second liquid tube 17, which through the control unit communicates directly with the first liquid tube 5.

The lid 3 is reversible, i.e. it may be turned around allowing the reservoir 4 to be formed in both positions of the lid.

FIG. 1 shows the lid in its storage position. In this the position the first liquid tube 5 and the first fluid tube 13a extend from its respective first and second through going holes towards the pump unit 9 into the reservoir.

When the anal irrigation system is to be used the lid is taken off as can be seen in FIG. 2, and the first liquid tube is pulled through the first through going hole. The first liquid tube is pulled so far that it extends in a length on the opposite side of the lid from the pump unit 9 corresponding to the depth of the container.

The tubes, the pump unit and the catheter are subsequently taken out from the container, and water or other irrigation liquid may be poured into the container.

The lid is then turned around and put on the container so that the length of the first liquid tube extending on the opposite side of the lid relative to the pump unit extends into the reservoir and into the irrigation fluid. This is the use position of the lid, wherein the anal irrigation system is ready to be used, which is shown in FIG. 3.

When used, which is not shown in the drawings, the balloon catheter is 15 is inserted into the rectum. The control unit 12 is set to its second position, such that when the user operates the manual pump 11 the balloon 14 expands whereby the balloon catheter is held in place in the rectum.

The control unit is then set to its first position. Thus, when the manual pump is operated air is pumped into the reservoir through the first fluid tube 13a. This builds up a pressure within the reservoir. The pressure pushes the irrigation fluid up through the first liquid tube, through the second liquid tube and out into the rectum via the balloon catheter.

The container may furthermore be provided with a rim 18 which can be used to hang the container on an edge if a table or other object while anal irrigation is performed.

Figure 4:
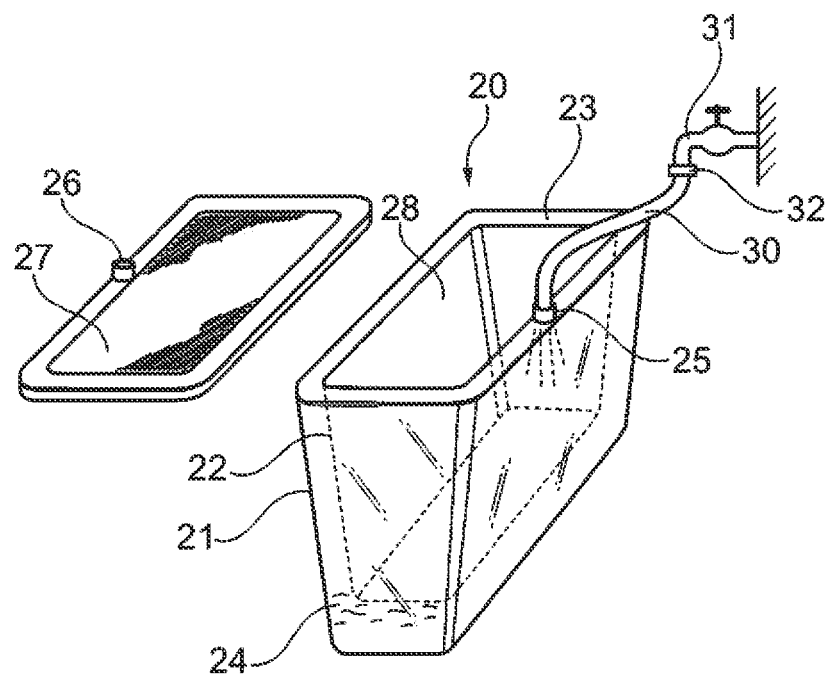
FIG. 4-7 shows a second embodiment of a container according to the invention in different configurations.
Figure 5:
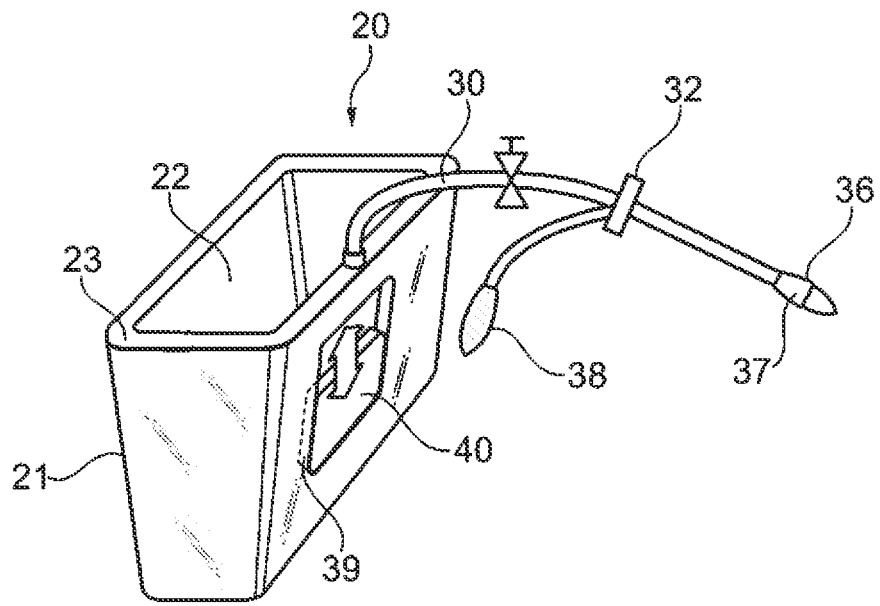

FIG. 4 shows another embodiment of a container 20 according to the invention. The container has an outer wall 21 and an inner wall 22. The inner wall has basically the same contour and shape as the outer wall but with smaller dimension so that it fits within the chamber defined by the outer wall. The outer wall and inner are fixed in their position relative to each other by a round going bridge element 23. Thus, a reservoir 24 is effectively defined between the outer wall, the inner wall and the bridge element. A closable opening 25 is provided for access to the reservoir.

The opening is closable by providing a sealing plug 26 on the bottom of a lid 27. Thus, the lid can be used to close the opening 25 is the plug is inserted therein. At the same time the lid covers the inner wall, thus covering a storage chamber 28 defined by the inner wall. The storage chamber can be used for storing the rest of the anal irrigation system during storage and transport.

Thus, irrigation fluid may be filled into the reservoir through the closable opening. This may be done through a liquid tube 30 which can be inserted into the closable opening or alternatively attached to the closable opening. As can be seen in FIG. 1 a typically faucet 31 may be used to fill the reservoir through the liquid tube 30. A connector element 32 is used to easily connect the liquid tube with the faucet.

After the reservoir has been filled, e.g. with one liter which is a typical volume used for anal irrigation, the faucet us disconnected from the connector element.

An anal probe 35 may then be connected to the liquid tube via the connector element. The anal probe comprises a balloon catheter 36. The balloon 37 on the balloon catheter is expandable by using a manual pump 38.

Figure 6:
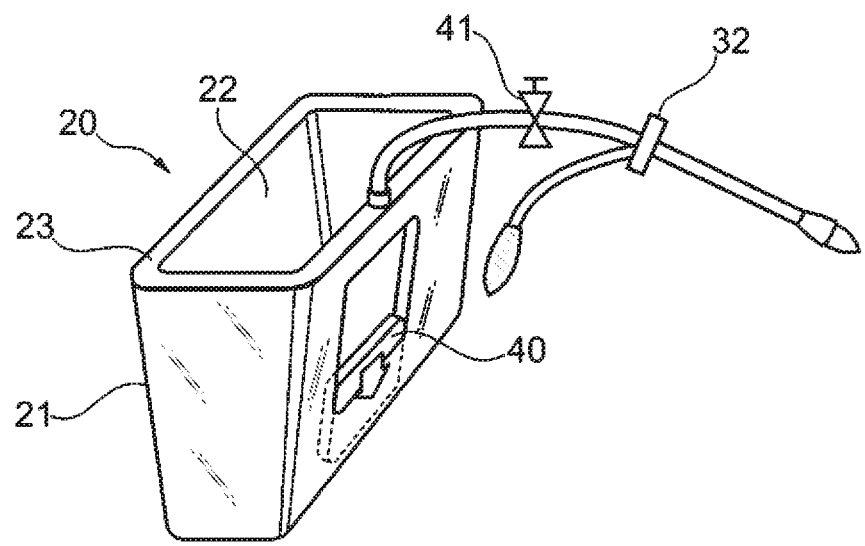
Figure 7:
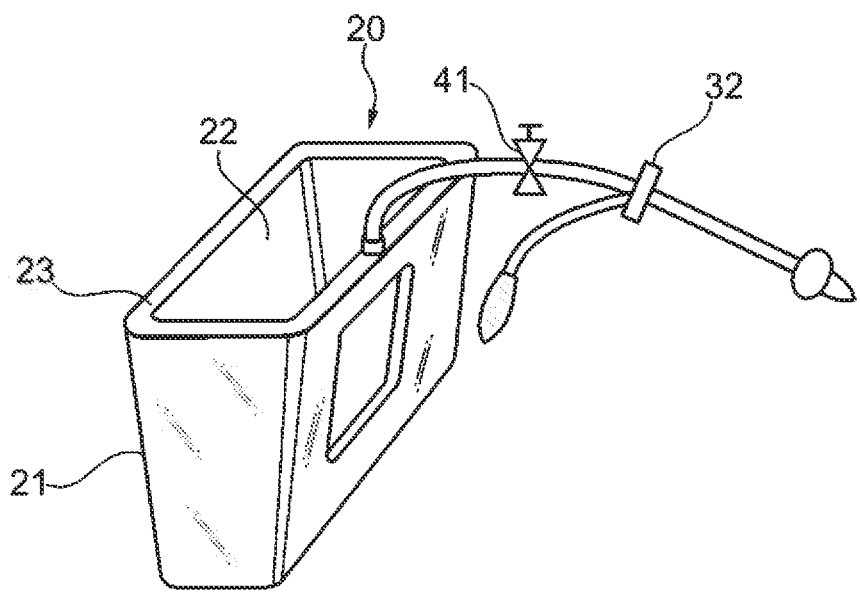

A pump 39 is provided on the container. The pump functions by displacing a pump element 40 into the reservoir (as shown in FIG. 6). Thus by displacing the irrigation fluid a pressure is built within the reservoir, which will force the irrigation fluid within the reservoir out through the liquid tube and into the rectum via the anal probe.

A valve 41 is provided on the liquid hose for controlling the flow of irrigation liquid.

When comparing the reservoir 24 of the second embodiment of a container 20 with the reservoir 4 of the first embodiment of a container it can be understood that the surface of the irrigation liquid in the second embodiment is smaller than the surface of the irrigation liquid in the first embodiment. Thus, seeing as pressure (p) equals to force (F) per area (a) (p=F/a) it will for the pressure be exerted a greater force if the area is smaller. In other words, in order to provide a water column, which is a meter and a half in the liquid tube (normal working conditions), less pressure has to be used in the reservoir according to the second embodiment for the same volume of liquid.

Accordingly, in order to benefit from the ease of use by using a reversible lid and the advantage of a smaller surface are of the irrigation liquid the first and second embodiments may of course be combined.

It should be understood that the pumps used herein may be manual, e.g. using the pumping action of an enclosed foam or a balloon. However, they may also be electrical so that a user only has to manually turn a switch on/off. Even further, the electrical pump may be automated, i.e. it may turn itself off when a certain pressure is achieved or pump in specific sequences etc.

The invention claimed is:

1. A container for an anal irrigation system, said anal irrigation system further comprising an anal probe,
a reservoir for holding an irrigation liquid, a pump mechanism for pumping a fluid into the reservoir, and a liquid tube connected to the pump mechanism and connecting the reservoir with the anal probe, wherein said container comprises, an outer chamber wall at least partly defining the reservoir, a lid for at least partly closing one end of said container thereby defining the reservoir, a first through going hole provided in the lid, wherein the liquid tube is slideably coupled in the first through going hole in a liquid tight manner, and a second opening providing fluid communication between the pump mechanism and the reservoir, wherein the lid is reversible and attachable to the container and configured to provide a storage configuration with the liquid tube slideably coupled in the first through going hole and the pump mechanism to be retained inside the container between the outer chamber wall and the lid.

2. A container according to claim 1, wherein a first end of the liquid tube is attached around the first through going hole on one side of the lid.

3. A container according to claim 1, wherein the lid is attachable to the container to provide an irrigation configuration with the liquid tube slideably coupled in the first through going hole and the pump mechanism positioned outside of the container.

* * * * *